US008258256B2

(12) United States Patent
Denmeade et al.

(10) Patent No.: US 8,258,256 B2
(45) Date of Patent: Sep. 4, 2012

(54) COMPOSITIONS AND METHODS FOR THE TREATMENT OF CANCER

(75) Inventors: Samuel R. Denmeade, Ellicot City, MD (US); Saurabh Aggarwal, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 137 days.

(21) Appl. No.: 12/087,400

(22) PCT Filed: Jan. 5, 2007

(86) PCT No.: PCT/US2007/000194
§ 371 (c)(1),
(2), (4) Date: Mar. 23, 2009

(87) PCT Pub. No.: WO2007/081751
PCT Pub. Date: Jul. 19, 2007

(65) Prior Publication Data
US 2009/0274625 A1 Nov. 5, 2009

Related U.S. Application Data

(60) Provisional application No. 60/756,293, filed on Jan. 5, 2006.

(51) Int. Cl.
*C07K 5/00* (2006.01)
*A61K 38/00* (2006.01)
(52) U.S. Cl. .......................... 530/300; 530/333; 514/1.1
(58) Field of Classification Search ........................ None
See application file for complete search history.

(56) References Cited

U.S. PATENT DOCUMENTS

2003/0129193 A1* 7/2003 Thorpe et al. .............. 424/155.1

FOREIGN PATENT DOCUMENTS

| WO | WO00157069 | * | 8/2001 |
| WO | WO03026590 | * | 4/2003 |

OTHER PUBLICATIONS

Sequence search result 2010.*
Simth et al , Chem Rev, vol. 97, p. 391-410, 2008.*
Bander NH, et al. Phase I trial of $^{177}$lutetium-labeled J591, a monoclonal antibody to prostate-specific membrane antigen, in patients with androgen-independent prostate cancer. J Clin Oncol. Jul. 20, 2005;23(21):4591-601.
Carter RE, et al. Prostate-specific membrane antigen is a hydrolase with substrate and pharmacologic characteristics of a neuropeptidase. Proc Natl Acad Sci U S A. Jan. 23, 1996;93(2):749-53.
Chang SS, et al. Five different anti-prostate-specific membrane antigen (PSMA) antibodies confirm PSMA expression in tumor-associated neovasculature. Cancer Res. Jul. 1, 1999;59(13):3192-8.
Cunha AC, et al. Tissue-specificity of prostate specific antigens: comparative analysis of transcript levels in prostate and non-prostatic tissues. Cancer Lett. May 18, 2006;236(2):229-38.
Davis MI, et al. Crystal structure of prostate-specific membrane antigen, a tumor marker and peptidase. Proc Natl Acad Sci U S A. Apr. 26, 2005;102(17):5981-6.
Dumas F, et al. Molecular expression of PSMA mRNA and protein in primary renal tumors. Int J Cancer. Mar. 15, 1999;80(6):799-803.
Fair WR, et al. Prostate-specific membrane antigen. Prostate. Jul. 1, 1997;32(2)140-8.
Grifman M, et al. Incorporation of tumor-targeting peptides into recombinant adeno-associated virus capsids. Mol Ther. Jun. 2001;3(6):964-75.
Huang X, et al. Anti-tumor effects and lack of side effects in mice of an immunotoxin directed against human and mouse prostate-specific membrane antigen. Prostate. Sep. 15, 2004;61(1):1-11.
Gala JL, et al. Expression of prostate-specific membrane antigen in transitional cell carcinoma of the bladder: prognostic value? Clin Cancer Res. Oct. 2000;6(10):4049-54.
Kawakami M, et al. Enhanced expression of prostate-specific membrane antigen gene in prostate cancer as revealed by in situ hybridization. Cancer Res. Jun. 15, 1997;57(12):2321-4.
Liu H, et al. Monoclonal antibodies to the extracellular domain of prostate-specific membrane antigen also react with tumor vascular endothelium. Cancer Res. Sep. 1, 1997;57(17):3629-34.
Mhaka A, et al. Use of methotrexate-based peptide substrates to characterize the substrate specificity of prostate-specific membrane antigen (PSMA). Cancer Biol Ther. Jun. 2004;3(6):551-8.
Oliver AJ, et al. Conformational and SAR analysis of NAALADase and PSMA inhibitors. Bioorg Med Chem. Oct. 1, 2003;11(20):4455-61.
O'Keefe DS, et al. Comparative analysis of prostate-specific membrane antigen (PSMA) versus a prostate-specific membrane antigen-like gene. Prostate. Feb. 1, 2004;58(2):200-10.
Parker SL, et al. Cancer statistics, 1997. CA Cancer J Clin. Jan.-Feb. 1997;47(1):5-27. Erratum in: CA Cancer J Clin Mar.-Apr. 1997;47(2):68.
Schülke N, et al. The homodimer of prostate-specific membrane antigen is a functional target for cancer therapy. Proc Natl Acad Sci U S A. Oct. 28, 2003;100(22):12590-5.
Silver DA, et al. Prostate-specific membrane antigen expression in normal and malignant human tissues. Clin Cancer Res. Jan. 1997;3(1):81-5.
Tiffany CW, et al. Characterization of the enzymatic activity of PSM: comparison with brain NAALADase. Prostate. Apr. 1, 1999;39(1):28-35.
Exhibit A: Ph.D. Phage Display Libraries-Instruction Manual. New England BioLabs (Ipswich, MA). pp. 4-5, Jun. 2011.

* cited by examiner

*Primary Examiner* — Lei Yao
(74) *Attorney, Agent, or Firm* — Edwards Wildman Palmer LLP; Peter F. Corless; Melissa Hunter-Ensor, Esq.

(57) ABSTRACT

The instant invention provides methods and compositions for the treatment and diagnosis of cancer, e.g., cancers characterized by the expression of prostate specific membrane antigen (PSMA).

12 Claims, 6 Drawing Sheets

Figure 1:
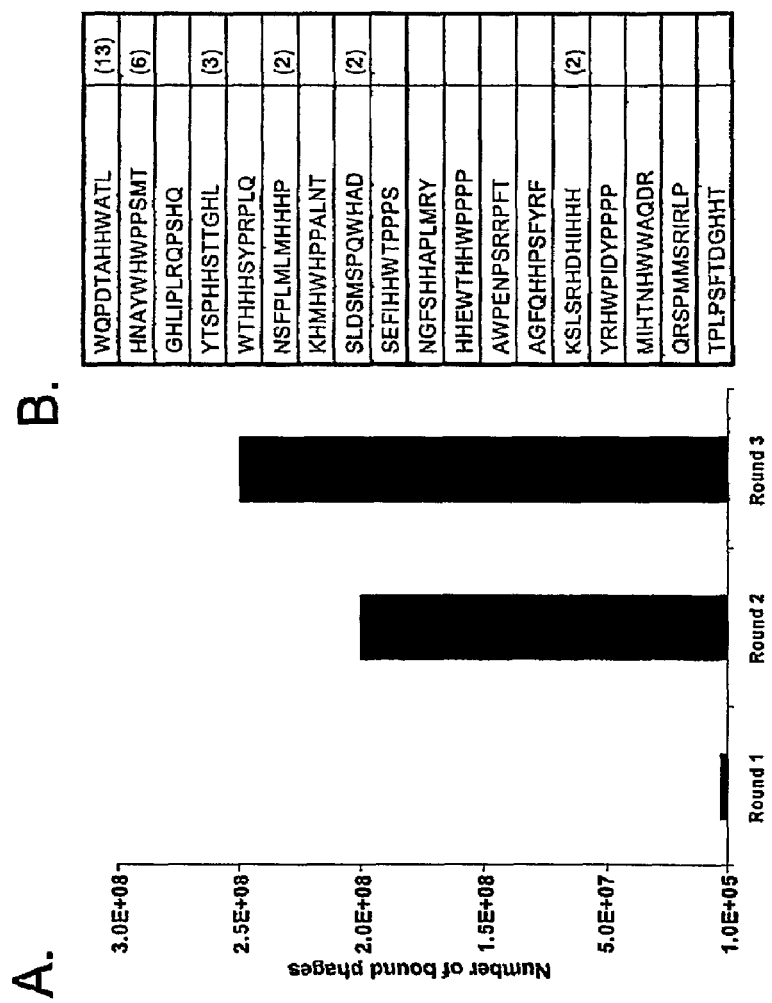

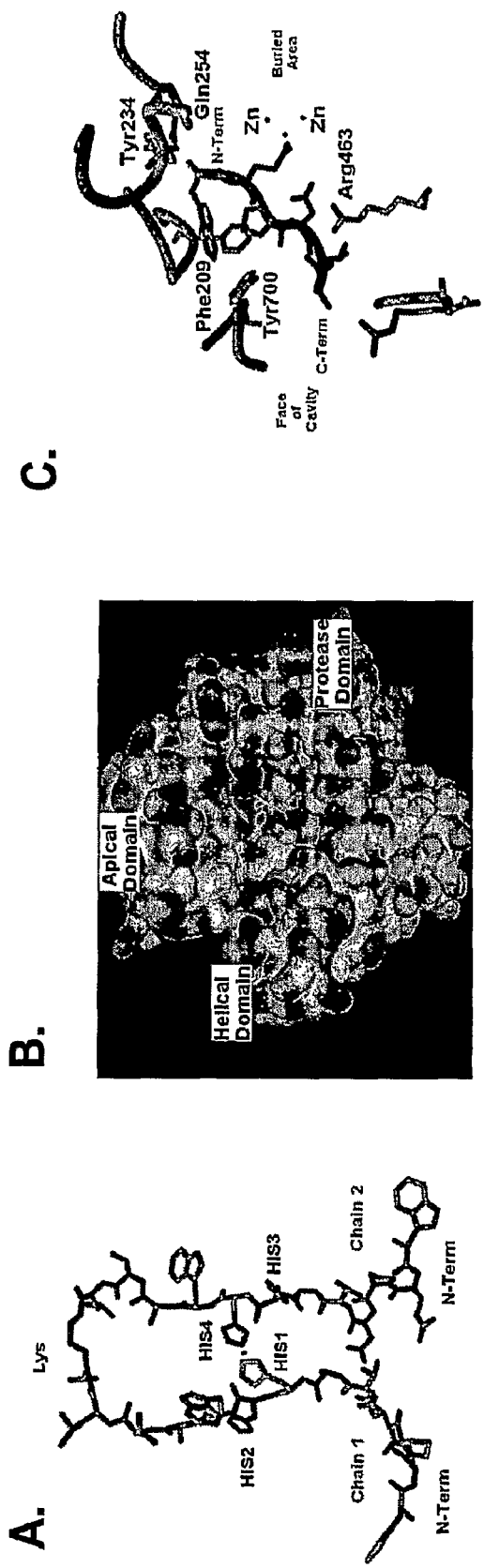
Figures 6A-C

SEQUENCE LISTING

```
<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Gln Pro Asp Thr Ala His His Trp Ala Thr Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

His Asn Ala Tyr Trp His Trp Pro Pro Ser Met Thr
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly His Leu Ile Pro Leu Arg Gln Pro Ser His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Thr Ser Pro His His Ser Thr Thr Gly His Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Thr His His His Ser Tyr Pro Arg Pro Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Ser Phe Pro Leu Met Leu Met His His His Pro
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys His Met His Trp His Pro Pro Ala Leu Asn
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Ser Leu Asp Ser Met Ser Pro Gln Trp His Ala Asp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Glu Phe Ile His His Trp Thr Pro Pro Pro Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Gly Phe Ser His His Ala Pro Leu Met Arg Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His Glu Trp Thr His His Trp Pro Pro Pro
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Trp Pro Glu Asn Pro Ser Arg Arg Pro Phe
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gly Phe Gln His His Pro Ser Phe Tyr Arg Phe
1               5                   10

<210> SEQ ID NO 14
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Ser Leu Ser Arg His Asp His Ile His His His
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Arg His Trp Pro Ile Asp Tyr Pro Pro Pro
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Ile His Thr Asn His Trp Trp Ala Gln Asp
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Arg Ser Pro Met Met Ser Arg Ile Arg Leu Pro
1               5                   10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      5x His tag

<400> SEQUENCE: 18

His His His His His
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Leu Ala Lys Leu Ala Lys Lys Leu Ala Lys Leu Ala Lys
1               5                   10
```

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaagatctc atcatcatca ccatcaccat aaatcctcca atgaagc                47

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcctcgagt cattaggcta cttcactcaa ag                                32

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Met Ala Arg Ile Pro Lys Arg Leu Ala Arg His
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Gln Pro Asp Thr Ala
1               5

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 25

```
His His His His His His
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His His Trp Ala
1

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His His Trp Ala Thr Leu
1               5

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Met Ala Arg Ile Pro Lys Arg Leu Ala Arg His Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly His Leu Ile Pro Leu Arg Gln Pro Ser His Gln
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Thr His His His Ser Tyr Pro Arg Pro Leu Gln
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 31

Lys His Met His Trp His Pro Pro Ala Leu Asn Thr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

His His Glu Trp Thr His His Trp Pro Pro Pro Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Trp Pro Glu Asn Pro Ser Arg Arg Pro Phe Thr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Arg His Trp Pro Ile Asp Tyr Pro Pro Pro Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Met Ile His Thr Asn His Trp Trp Ala Gln Asp Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Pro Leu Pro Ser Phe Thr Asp Gly His His Thr
1               5                   10

<210> SEQ ID NO 37
<211> LENGTH: 13
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Gln Pro Asp Thr Ala His His Trp Ala Thr Leu Lys
1               5                   10
```

COMPOSITIONS AND METHODS FOR THE TREATMENT OF CANCER

RELATED APPLICATIONS

This applications claims the benefit of U.S. Provisional Application No. 60/756,293, filed Jan. 5, 2006, the entire contents of which is hereby incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 7, 2011, is named 67095.txt and is 9,339 bytes in size.

BACKGROUND OF THE INVENTION

Cancer cells may be are defined by two heritable properties, uncontrolled growth and uncontrolled invasion of normal tissue. A cancerous cell can divide in defiance of the normal growth constraints in a cell leading to a localized growth or tumor. In addition, some cancer cells may become metastatic, gaining the ability to migrate away from their initial site and invade other tissues areas and types. It is the combination of these two features that make a cancer cell especially dangerous.

As determined from epidemiological and clinical studies, most cancers develop in slow stages from mildly benign into malignant neoplasms. Malignant cancer usually begins as a benign localized cell population with abnormal growth characteristics called dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the clearest examples of the progression of normal tissue to benign neoplasm to malignant neoplasm.

Prostate cancer is the most common malignancy in men in the USA, resulting in an estimated 41,800 deaths in 1997 (Parker S L, et al., C A Cancer J Clin 47: 5-27, 1997). The widespread use of prostate-specific antigen (PSA) has dramatically increased the number of patients diagnosed with prostate cancer and generally lowered the stage of disease at diagnosis. (Scardino P T, Urol. Clin. N. Am. 16:635-655, 1989; Epstein J L, et al., JAMA 271: 368-374, 1994). Nevertheless, 5%-10% of cancers detected by PSA screening are clinically advanced and not candidates for radical prostatectomy. Despite surgical removal of the prostate, 30%-60% of men treated will have recurrence of cancer within 5 years, suggesting that the clinical stage of the patients undergoing surgery was highly inaccurate. 20%-57% of patients undergoing definitive surgery with presumed localized disease will have rising PSA following treatment, also indicative of local or distant residual disease. (Ohori M, et al., J. Urol. 154: 1818-1824, 1995; Zeitman A L, et al., Urology 43: 828-833, 1994). Neither of these conditions is amenable to curative therapy.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma, a type of neoplasia. BPH is very common in men over the age of 50. It is characterized by the presence of a number of large distinct nodules in the periurethral area of the prostate.

Currently, there is a need in the art for more effective cancer therapeutics, e.g., prostate cancer therapeutics.

SUMMARY OF THE INVENTION

The instant invention is bases, at least in part, on the discovery of a number of peptides that specifically bind to prostate specific membrane antigen. Accordingly, the instant invention provides methods and compositions utilizing these peptides for the treatment and diagnosis of cancer.

In one embodiment, the invention provides peptides comprising the amino acid sequence set forth as any one of SEQ ID NO:1-SEQ ID NO:17, wherein the peptide is capable of binding to PSMA. In a specific embodiment, the peptide comprises the amino acid set forth as SEQ ID NO:1.

In another embodiment, the peptide consists of the amino acid set forth as SEQ ID NO:1. In another specific embodiment, the peptide comprises the amino acid set forth as SEQ ID NO:1. In another embodiment, the peptide further comprises a second amino acid sequence set forth as SEQ ID NO:1. In a related embodiment, the peptide further comprising one or more additional amino acid sequences set forth as SEQ ID NOs:1-17.

In another embodiment, the peptide consists of the amino acid set forth as SEQ ID NO:2. In another embedment, the peptide further comprises a second amino acid sequence set forth as SEQ ID NO:2. In another embodiment, the peptide comprises one or more additional amino acid sequences set forth as SEQ ID NOs:1-17.

In one aspect, the invention provides peptides comprising a first amino acid sequence selected from the group consisting of SEQ ID NO:1-17 and a second amino acid sequence selected from the group consisting of SEQ ID NO:1-17, wherein the first and second amino acid sequences are connected by a linker. In one embodiment, the first and second amino acid sequences are the same amino acid sequences. In another embodiment, the first and second amino acid sequences are different amino acid sequences. In one embodiment, the peptide comprises a first amino acid sequence as set forth in SEQ ID NO:1 and a second amino acid sequence as set forth in SEQ ID NO:1, wherein the first and second amino acid sequences are connected by a linker, e.g., an amino acid, peptide, chemical moiety, diamine, or polyglycol. In a specific embodiment, the linker is a lysine residue or polylysine peptide. An exemplary peptide of the invention comprises two amino acid sequences set forth as SEQ ID NO:1 connected by a lysine linker (as set forth in FIG. 3B).

In related embodiment, the peptides of the invention further comprise an anticancer agent, e.g., a chemotherapeutic agent such as thapsigargin, doxorubicin, or derivatives thereof. The anticancer agent can also be a peptide toxin, e.g., KLAKLAKKLAKLAK (SEQ ID NO:19), a protein toxin, e.g., proaerolysin or shiga toxin. In another embodiment, the peptides may further comprises an imaging agent, e.g., a radiolabel.

In another aspect, the invention provides prodrugs comprising the peptides of the invention and an anticancer agent, e.g., a chemotherapeutic agent such as thapsigargin, doxorubicin, or derivatives thereof. The anticancer agent can also be a peptide toxin, e.g., KLAKLAKKLAKLAK (SEQ ID NO:19), a protein toxin, e.g., proaerolysin or shiga toxin.

In another aspect, the invention provides methods of treating a subject having cancer by administering to the subject a peptide or prodrug of the invention, thereby treating the subject. In one embodiment, the cancer is a is a solid tumor cancer. In another embodiment, the cancer is characterized by cells expressing PSMA. In specific embodiments, the cancer is selected from the group consisting of prostate, breast, colon, lung, brain, kidney, and bladder cancer.

In another aspect, the invention provides methods of determining if a subject has cancer by administering to the subject a composition comprising the a peptide of the invention and an imaging agent and obtaining an image of the subject, thereby determining if the subject has cancer.

In one embodiment, the cancer is a is a solid tumor cancer. In another embodiment, the cancer is characterized by cells expressing PSMA. In specific embodiments, the cancer is selected from the group consisting of prostate, breast, colon, lung, brain, kidney, and bladder cancer.

In another aspect, the invention provides pharmaceutical compositions comprising a one or more peptides and/or prodrugs of the invention and a pharmaceutically acceptable carrier.

In another aspect, the invention provides kits for the treatment of cancer comprising the one or more peptides and/or prodrugs of the invention and instructions for use.

In another aspect, the invention provides kits for the detection of cancer comprising the one or more peptides and/or prodrugs of the invention and instructions for use.

I. DESCRIPTION OF THE DRAWINGS

FIGS. 1A-B depict the enrichment of phages binding to PSMA over three rounds of selection. (A) Number of phage bound after each round of selection. (B) Single letter amino acid sequence of the random insert from each selected phage (SEQ ID NOS 1-2, 29, 4, 30, 6, 31, 8-10, 32-33, 13-14, 34-35, 17 and 36, respectively, in order of appearance). Number in parentheses indicates number of phage from sequenced pool (n=40) containing the unique sequence.

Figure 2:
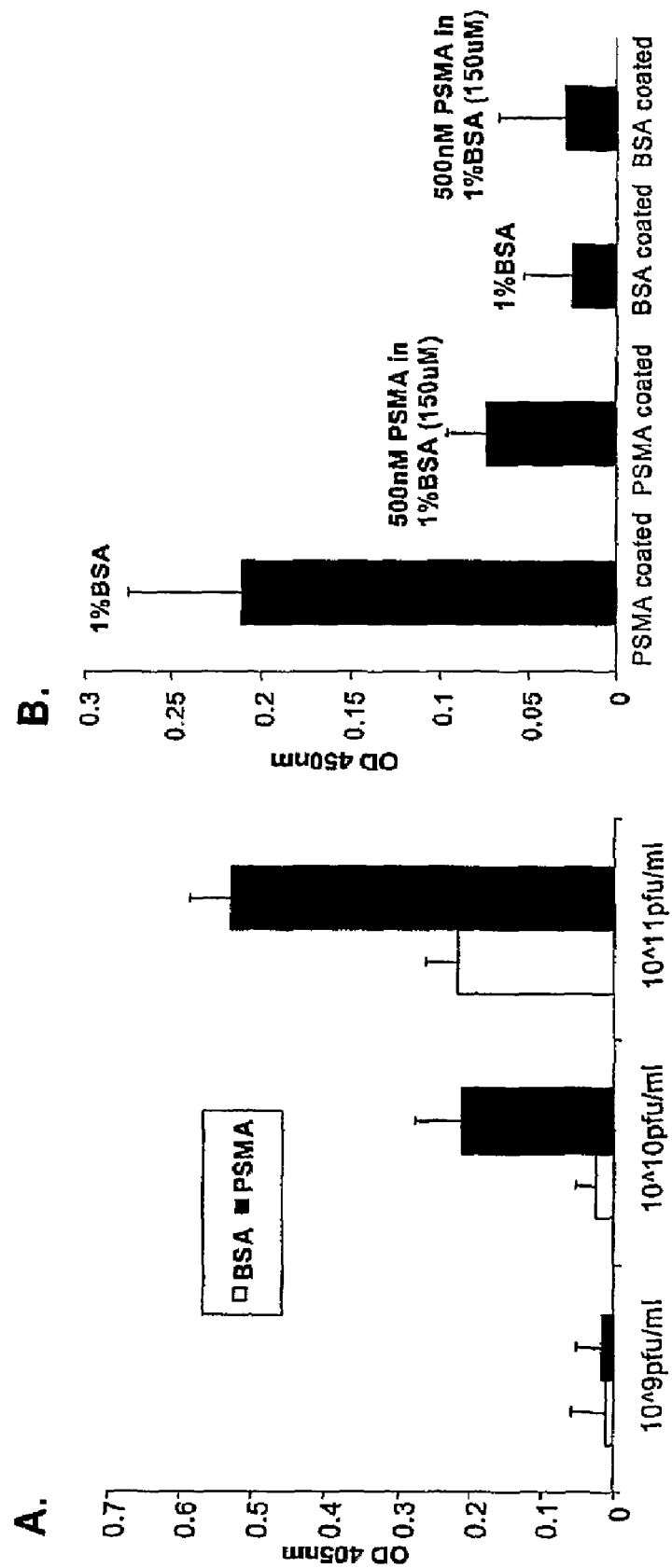

FIGS. 2A-B depict the binding of phage with peptide sequence WQPDTAHHWATL (SEQ ID NO:1) to BSA and PSMA. Recombinant PSMA (0.625 µgs) in BSA (25 µgs/ml) or BSA alone was immobilized and indicated dilutions of phages were incubated with immobilized proteins. Extent of binding of Anti-M13 antibody to phage bound to PSMA or BSA was determined by addition of HRP substrate OPD and measurement of absorbance at 450 nm (A). Competitive inhibition with soluble PSMA of WQPDTAHHWATL (SEQ ID NO:1) phage binding to immobilized PSMA. Soluble PSMA (500 nM) was used to compete with PSMA-binding phages containing the WQPDTAHHWATL (SEQ ID NO:1) peptide at concentration of $10^{10}$ pfu/ml phage (B). Results are the mean binding in 4 replicate wells each ±S.D.

Figure 3:
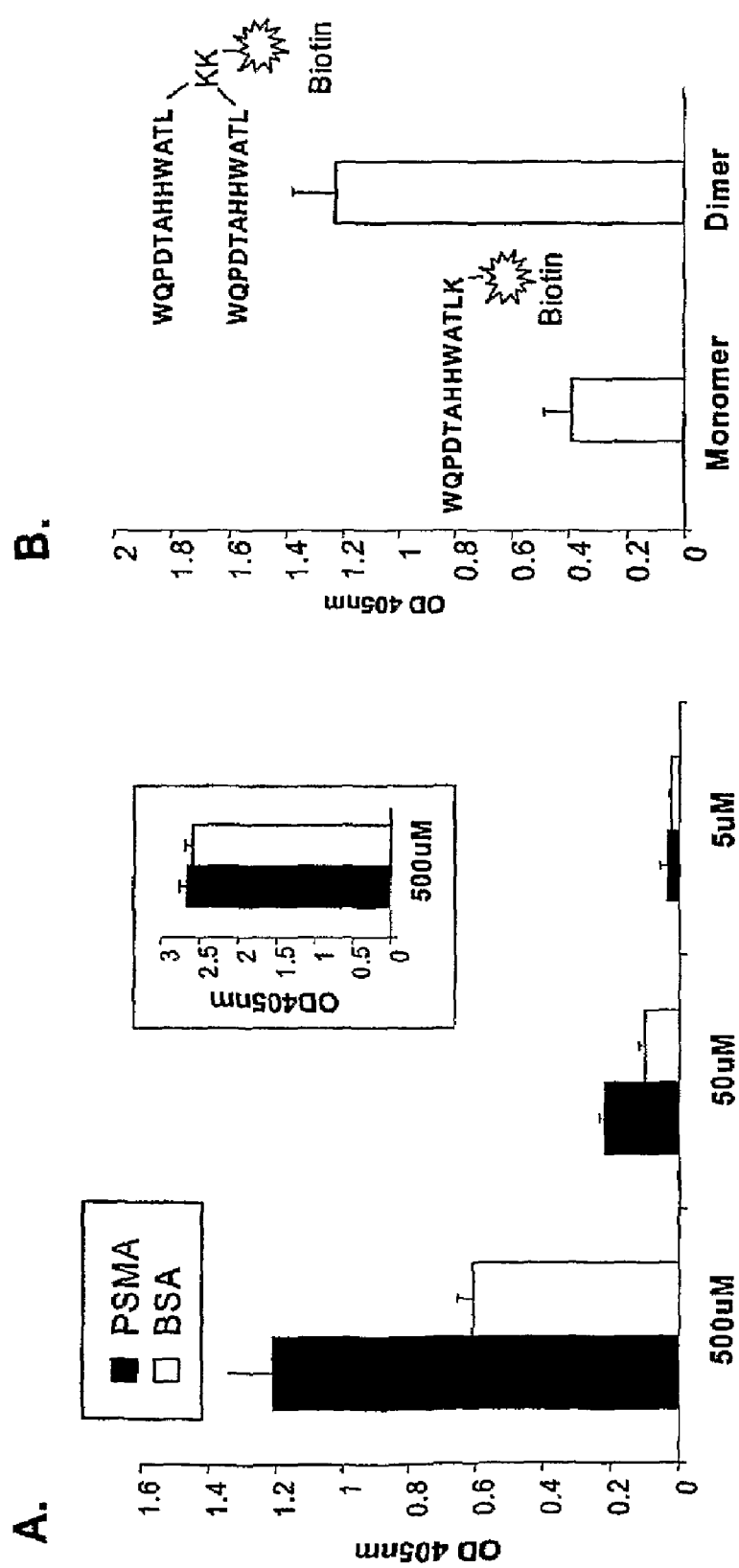

FIGS. 3A-B depict (A) Soluble WQPDTAHHWATLK (Biotin) (SEQ ID NO: 37) peptide binding to BSA and PSMA. Recombinant PSMA (0.625 µgs) and BSA (25 µgs/ml) were immobilized and indicated concentrations of the biotinylated WQPDTAHHWATL (SEQ ID NO:1) peptide were incubated with immobilized PSMA or BSA. Inset shows results from non-selected control peptide QMARIPKRLARHK-biotin (SEQ ID NO: 28) assayed for binding using same procedure. (B) Comparison of PSMA binding to monomeric (SEQ ID NO: 37) and dimeric (core peptide disclosed as SEQ ID NO: 1) form of the WQPDTAHHWATL (SEQ ID NO:1) peptide. Biotin labeled monomeric and dimeric peptide were immobilized on streptavidin-coated plates then incubated with His-PSMA (100 nM). Results are the mean binding in 4 replicate wells each ±S.D.

Figure 4:
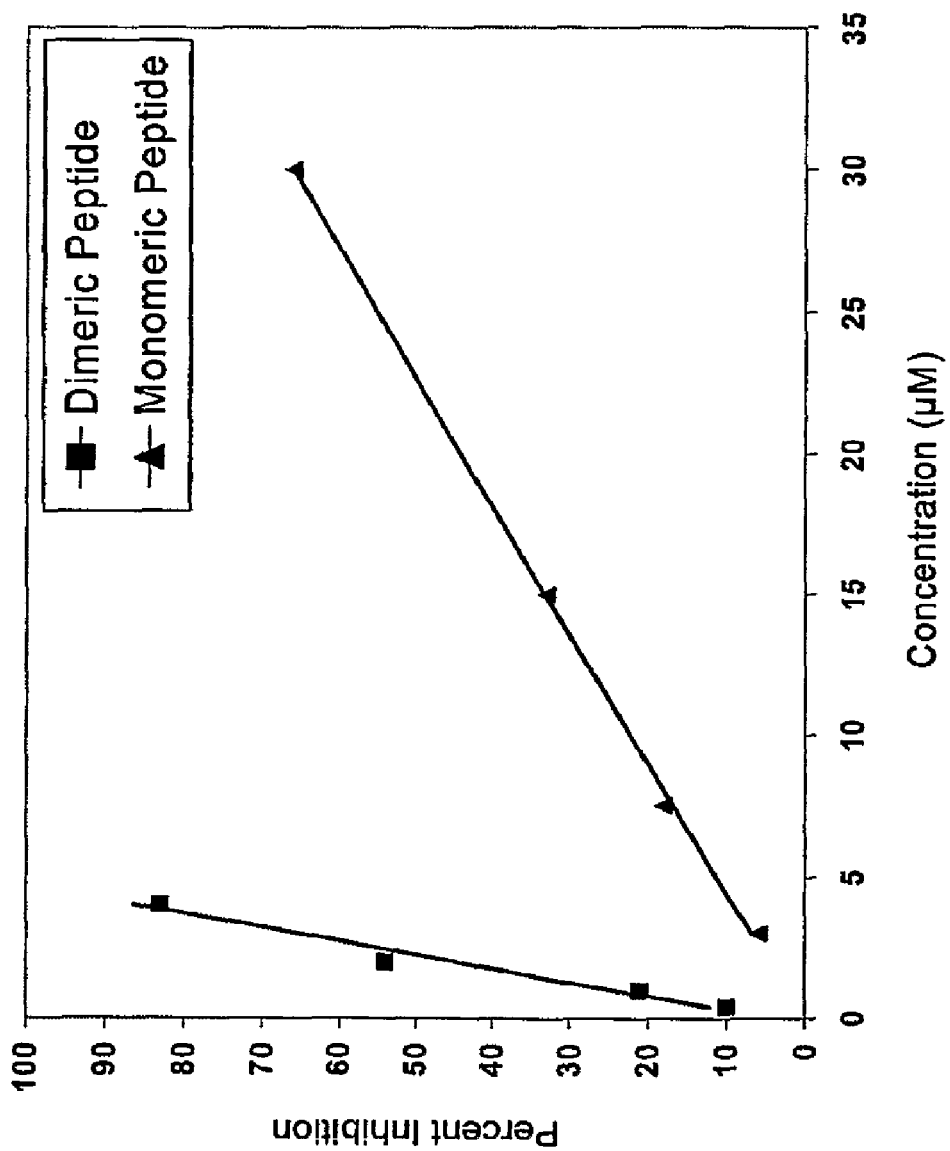

FIG. 4 depicts the inhibition of NAALADase activity of PSMA by monomeric and dimeric peptides. His-PSMA hydrolysis of $^3$H-NAAG was assayed as described in the methods in the absence or presence of indicated concentration of monomeric or dimeric peptide. After 15 min incubation at 37° C. amount of released 3H-Glu was determined. Percent inhibition is the ratio of amount of 3H-Glu released in presence of peptide compared to control (i.e. His-PSMA only). Data plotted are average of duplicate experiments and best fit line is included.

Figure 5:
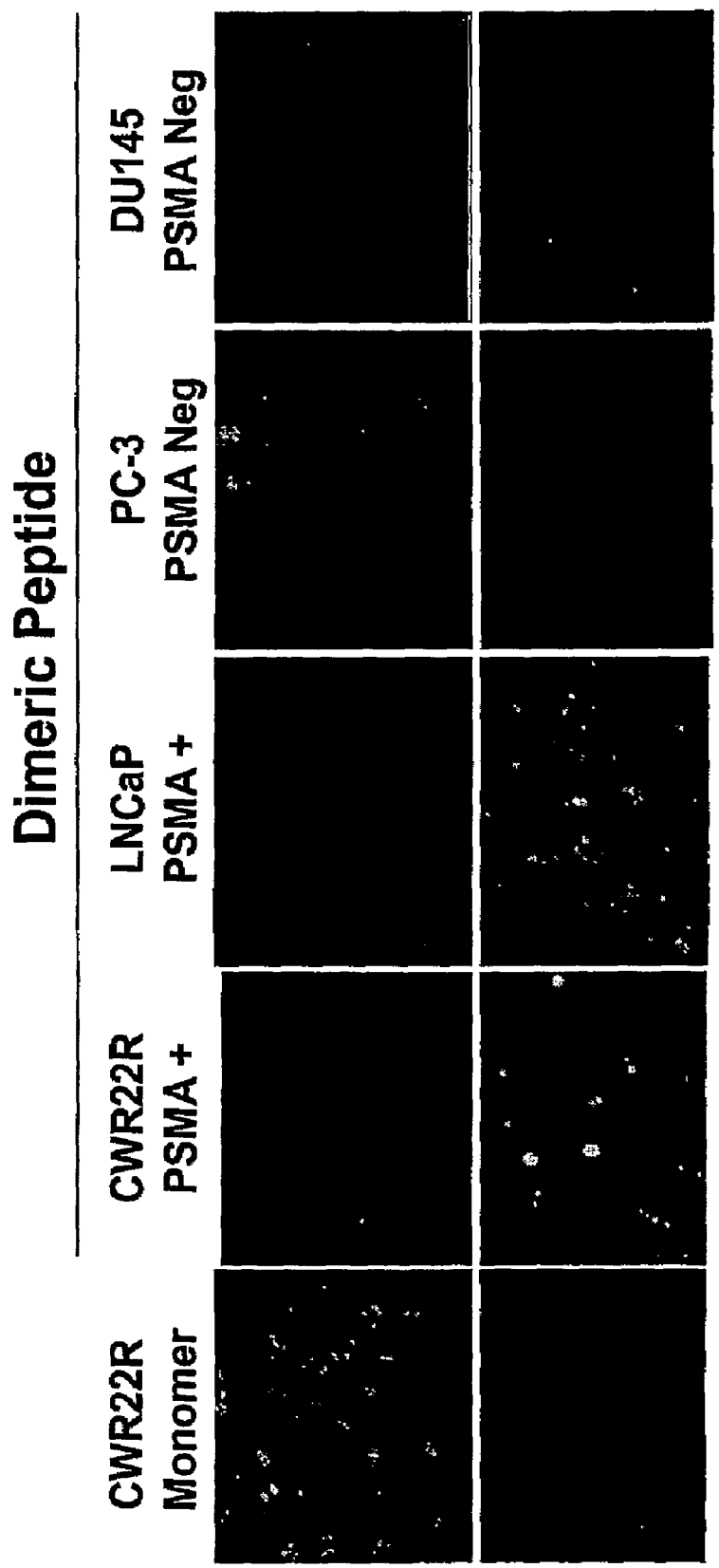

FIG. 5 depicts dimeric WQPDTAHHWATL (SEQ ID NO:1) peptide binds selectively to PSMA-producing prostate cancer cells. Attached PSMA-positive (LNCaP, CWR22R) and PSMA-negative (PC-3, DU145) human prostate cancer were prelabeled with Orange Cell Tracker (Invitrogen) at 2.5 µM in RPMI for 30 mins. After washing with Hanks balanced salt solution, cells were incubated with FITC-labeled monomeric (50 µM) or dimeric (5 µM) WQPDTAHHWATL (SEQ ID NO:1) peptide in 1% fetal calf serum containing media for 1 hr. Cells were washed 3 times with PBS and fixed with 1% Formalin for ½ hr at room temperature. Cells were visualized using Zeiss Meta 510 confocal microscope at 20× magnification. Top panels show orange cell tracker labeled cells (rhodamine filter set); middle panels show labeled peptide binding (FITC filter set); bottom panel show overlay of both panels.

FIGS. 6A-C depict (A) the solution structure of Dimeric Peptide (WQPDTAHHWATL)$_2$-K (core peptide disclosed as SEQ ID NO: 1). The metal coordinating Histidine residues are shows in yellow while the Histidines exposed to the solvent are shown in magenta. The Cobalt ion is shows in green. (B) The molecular surface representation of the PSMA catalytic site. The docked peptide moiety is shown in yellow while the protein residues interacting with the peptide are shown in white. (C) The binding mode of WQPDTA (SEQ ID NO: 23) peptide moiety. The W1, Q2, P3, D4, T5 and A6 are shown in yellow, green, orange, purple, blue and red respectively. The orientation of PSMA monomer is such that face of binding cavity is facing left, while the buried area at the bottom of catalytic side containing Zinc ions is on the right side.

DETAILED DESCRIPTION OF THE INVENTION

The instant invention is based, at least on part, on the discovery by the inventors of novel peptides that bind to PSMA. Based on this discovery, the instant invention provides methods and compositions for the treatment and diagnosis of cancer.

The term "contacting" refers to exposing tissue to the peptides, therapeutic drugs or prodrugs of the invention so that they can effectively inhibit cellular processes, or kill cells. Contacting may be in vitro, for example by adding the peptide, drug or prodrug to a tissue culture to test for susceptibility of the tissue to the peptide, drug or prodrug. Contacting may be in vivo, for example administering the peptide, drug, or prodrug to a subject with a cell or in vitro.

By "peptide" or "polypeptide" is meant any chain of amino acids, regardless of length or post-translational modification (e.g., glycosylation or phosphorylation). As written herein, amino acid sequences are presented according to the standard convention, namely that the amino-terminus of the peptide is on the left, and the carboxy terminus on the right.

A "detectable label" refers to a reporter molecule or enzyme that is capable of generating a measurable signal and is covalently or noncovalently joined to a polynucleotide or polypeptide.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating", "treat", or "treatment" embrace both preventative, e.g., prophylactic, and palliative treatment.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include prostate, breast, colon, lung, brain, kidney, and bladder cancer.

As used herein, the term "subject" refers to any animal (e.g., a mammal), including, but not limited to, humans, non-human primates, rodents, and the like (e.g., which is to be the recipient of a particular treatment, or from whom cancer stem cells are harvested). Typically, the terms "subject" and "patient" are used interchangeably, unless indicated otherwise herein.

As used herein, the term "subject is suspected of having cancer" refers to a subject that presents one or more signs or symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "subject at risk for cancer" refers to a subject with one or more risk factors for developing a specific cancer. Risk factors include, but are not limited to, gender, age, genetic predisposition, environmental expose, and previous incidents of cancer, preexisting non-cancer diseases, and lifestyle.

As used herein, the term "cancer cells" refers to individual cells of a cancer. Such cells may include, for example, cells that express prostate specific membrane antigen (PSMA).

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.) and the like.

As used herein, the term "co-administration" refers to the administration of at least two agent(s) or therapies to a subject. In some embodiments, the co-administration of two or more agents or therapies is concurrent In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

"Amino acid sequence" and terms such as "polypeptide" or "protein" are not meant to limit the amino acid sequence to the complete, native amino acid sequence associated with the recited protein molecule.

As used herein the term "prodrug" refers to a pharmacologically inactive derivative of a parent "drug" molecule that requires biotransformation (e.g., either spontaneous or enzymatic) within the target physiological system to release, or to convert (e.g., enzymatically, mechanically, electromagnetically, etc.) the "prodrug" into the active "drug." "Prodrugs" are designed to overcome problems associated with stability, toxicity, lack of specificity, or limited bioavailability. Exemplary "prodrugs" comprise an active "drug" molecule itself and a chemical masking group (e.g., a group that reversibly suppresses the activity of the "drug"). Some preferred "prodrugs" are variations or derivatives of compounds that have groups cleavable under metabolic conditions. Exemplary "prodrugs" become pharmaceutically active in vivo or in vitro when they undergo solvolysis under physiological conditions or undergo enzymatic degradation or other biochemical transformation (e.g., phosphorylation, hydrogenation, dehydrogenation, glycosylation, etc.). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Exemplary prodrugs of the invention comprise a PSMA specific peptide and an anticancer agent.

Peptides of the Invention

The instant invention provides peptides that are capable of binding to prostate-specific membrane antigen (PSMA). Exemplary peptides of the invention include WQPDTAHHWATL (SEQ ID NO:1), HNAYWHWPPSMT (SEQ ID NO:2), GHLIPLRQPSH (SEQ ID NO:3), YTSPHHSTGHL (SEQ ID NO:4), WTHHHSYPRPL (SEQ ID NO:5), NSFPLMLMHHHP (SEQ ID NO:6), KHMHWHPPALN (SEQ ID NO:7), SLDSMSPQWHAD (SEQ ID NO:8), SEFIHHWTPPPS (SEQ ID NO:9), NGFSHHAPLMRY (SEQ ID NO:10), HHEWTHHWPPP (SEQ ID NO:11), AWPENPSRRPF (SEQ ID NO:12), AGFQHHPSFYRF (SEQ ID NO:13), KSLSRHDHIHHH (SEQ ID NO:14), YRHWPIDYPPP (SEQ ID NO:15), MIHTNHWWAQD (SEQ ID NO: 16), QRSPMMSRIRLP (SEQ ID NO: 17).

In one embodiment the invention provides a peptide comprising the amino acid sequence WQPDTAHHWATL (SEQ ID NO:1). In another embodiment, the invention provides a peptide comprising the amino acid sequence HNAYWHWPPSMT (SEQ ID NO:2). The peptides of the invention may further comprise one or more anticancer or imaging agents for the treatment or diagnosis of cancer. The peptides of the invention may further be "dimers". "Dimers" of the invention provide two peptides of the invention connected by a linker, e.g., a peptide linker. An exemplary dimer of the invention is set forth in FIG. 3B. The peptides present in the dimer may be identical, e.g., two peptides of SEQ ID NO:1, or non-identical, e.g., one peptide having SEQ ID NO:1 and one peptide having SEQ ID NO:2.

Moreover, the peptides of the invention may be linear or cyclic. A "cyclic peptide" refers, in one instance, to a compound of the invention in which a ring is formed by the formation of a peptide bond between the nitrogen atom at the N-terminus and the carbonyl carbon at the C-terminus. "Cyclized" also refers to the forming of a ring by a covalent bond between the nitrogen at the N-terminus of the compound and the side chain of a suitable amino acid in the sequence present therein, preferably the side chain of the C-terminal amino acid. For example, an amide can be formed between the nitrogen atom at the N-terminus and the carbonyl carbon in the side chain of an aspartic acid or a glutamic acid. Alternatively, the compound can be cyclized by forming a covalent bond between the carbonyl at the C-terminus of the compound and the side chain of a suitable amino acid in the sequence contained therein, preferably the side chain of the N-terminal amino acid. For example, an amide can be formed between the carbonyl carbon at the C-terminus and the amino nitrogen atom in the side chain of a lysine or an ornithine. Additionally, the compound can be cyclized by forming an ester between the carbonyl carbon at the C-terminus and the hydroxyl oxygen atom in the side chain of a serine or a threonine.

"Cyclized" also refers to forming a ring by a covalent bond between the side chains of two suitable amino acids in the sequence present in the compound, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in the side chain of, for example, a lysine or an ornithine.

In addition, a compound can be cyclized with a linking group between the two termini, between one terminus and the side chain of an amino acid in the compound, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAI) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups.

Additionally, peptides of the invention may be cyclized by their interaction with, for example, divalent metal ions. These ions, e.g., divalent metal cations, may stabilize a cyclic conformation of the peptides of the invention when in solution, without having to covalently join the termini of the peptides.

Additionally, the peptides of the invention may contain one or more non-naturally occurring amino acid residue. The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids. Amino acid analogs are well-known in the art; a large number of these analogs are commercially available. Many times the use of non-naturally occurring amino acids in the peptide has the advantage that the peptide is more resistant to degradation by enzymes which fail to recognize them.

The term "conservative substitution" in the context of the present invention refers to the replacement of an amino acid present in the native sequence in the specific kinase with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the native amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound.

For example in accordance with the invention the following substitutions are considered as conservative: replacement of arginine by cytroline; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

"Peptidoniimetic organic moiety" can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However such similarities are not necessarily required. The only restriction on the use of peptidomimetics is that the compounds retain their tissue-remodeling modulating activity as compared to compounds constituting sequence regions identical to those appearing in the native kinase.

Peptidomimetics are often used to inhibit degradation of the peptides by enzymatic or other degradative processes. The peptidomimetics can be produced by organic synthetic techniques. Examples of suitable peptidomimetics include D amino acids of the corresponding L amino acids, tetrazol (Zabrocki et al, J Am. Chem. Soc. 110:5875-5880 (1988)); isosteres of amide bonds (Jones et al., Tetrahedron Lett. 29: 3853-3856 (1988)).

Linkers

The dimeric peptides of the invention may comprise a linker, e.g., a linker amino acid or peptide, located between two amino acid sequences of the invention. The linker can be of natural origin, such as a sequence determined to exist in random coil between two domains of a protein. In one embodiment, the linker is a lysine residue. Another exemplary linker sequence is the linker found between the C-terminal and N-terminal domains of the RNA polymerase a subunit. Other examples of naturally occurring linkers include linkers found in the 1cI and LexA proteins. Alternatively, the linker can be of synthetic origin. For instance, the sequence (Gly$_4$Ser)$_3$ (SEQ ID NO: 24) can be used as a synthetic unstructured linker. Linkers of this type are described in Huston et al. (1988) PNAS 85:4879; and U.S. Pat. No. 5,091,513.

Within the linker, the amino acid sequence may be varied based on the preferred characteristics of the linker as determined empirically or as revealed by modeling. For instance, in addition to a desired length, modeling studies may show that side groups of certain amino acids may interfere with the biological activity of the protein. Considerations in choosing a linker include flexibility of the linker, charge of the linker, and presence of some amino acids of the linker in the naturally-occurring subunits. For example, a linker may contain an amino acid sequence which can be recognized by a protease so that the activity of the peptide or protein could be regulated by cleavage.

In one embodiment of the invention, the linker may be a lysine residue or polylysine linker. The use of a polylysine linker would allow for the formation of higher order oligomers through attachment to the epsilon amine of the lysine residues. For example, a di-lysine linker can be used to form a peptide comprising four peptides of the invention.

Moreover, non-peptide linkers can be used in the compositions of the invention. For example, glycols such as polyethylene glycol and diamines are contemplated for use in the peptides of the instant invention.

Production of Peptides of the Invention

Expression, isolation, synthesis and purification of the peptides of the invention may be accomplished by any suitable technique, including but not limited to the following.

Expression vectors comprising DNA may be used to prepare the peptides of the invention. A method for producing peptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and the characteristics of the given peptide.

Any suitable expression system may be employed. The vectors include a DNA encoding a peptide of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

Peptide of the present invention may be synthesized by solid phase peptide synthesis (e.g., t-BOC or F-MOC) method, by solution phase synthesis, or by other suitable techniques including combinations of the foregoing methods. The t-BOC and F-MOC methods, which are established and widely used, are described in Merrifield, J. Am. Chem. Soc. 88:2149 (1963); Meienhofer, Hormonal Proteins and Peptides, C. H. Li, Ed., Academic Press, 1983, pp. 48-267; and Barany and Merrifield, in The Peptides, E. Gross and J. Meienhofer, Eds., Academic Press, New York, 1980, pp. 3-285. Methods of solid phase peptide synthesis are described in Merrifield, R. B., Science, 232: 341 (1986); Carpino, L. A. and Han, G. Y., J Org. Chem., 37: 3404 (1972); and Gauspohl, H. et al, Synthesis, 5:315 (1992)).

Moreover, peptides of the invention may produced in a subject using a number of well known techniques. Accordingly, the instant invention further relates to the use of a nucleic acid molecule encoding a peptide of the invention for the treatment of caner and for the manufacture of a medicament for the treatment of cancer.

In one embodiment, a nucleic acid molecule encoding a peptide of the invention is introduced in vivo in a viral vector. Such vectors include an attenuated or defective DNA virus, such as, but not limited to, herpes simplex virus, papilloma virus, Epstein-Barr virus, adenovirus, adeno-associated virus, and the like. The effective viruses which entirely or almost entirely lack viral genes are preferred. A defective virus is not effective after the introduction into a cell. Use of defective viral vectors allows for administration to cells in a specific, localized area, without concern that the vector can infect other cells. Examples of particular vectors include, but are not limited to, a defective herpes simplex virus I vector (Kaplitt et al., Molec. Cell. Neurosci. 2:320-30, 1991); an attenuated adenovirus vector, such as the vector described by Strafford-Perricaudet et al., J. Clin. Invest. 90:626-30, 1992; and a defective adeno-associated virus vector (Samulski et al., J. Virol. 61:3096-101, 1987; Samulski et al., J. Virol. 63:3822-8, 1989).

In another embodiment, a nucleic acid can be introduced in a retroviral vector, e.g., as described in Anderson et al., U.S. Pat. No. 5,399,346; Mann et al. Cell 33:153, 1983; Temin et al., U.S. Pat. No. 4,650,764; Temin et al., U.S. Pat. No. 4,980,289; Markowitz et al., J. Virol. 62:1120, 1988; Temin et al., U.S. Pat. No. 5,124,263; WO 95/07358; and Kuo et al., Blood 82:845, 1993. Alternatively, the vector can be introduced by lipofection in vivo using liposomes. Synthetic cationic lipids can be used to prepare liposomes for in vivo transfection of one or more anticancer agents (Felgner et al., Proc. Natl. Acad. Sci. USA 84:7413-7, 1987; Mackey et al., Proc. Natl. Acad. Sci. USA 85:8027-31, 1988).

Anticancer Agents

As used herein, the terms "drug", "chemotherapeutic agent" and "anticancer agent" refer to pharmacologically active molecules that are used to diagnose, treat, or prevent diseases or pathological conditions in a physiological system (e.g., a subject, or in vivo, in vitro, or ex vivo cells, tissues, and organs). Drugs act by altering the physiology of a living organism, tissue, cell, or in vitro system to which the drug has been administered. It is intended that the terms "drug" and "chemotherapeutic agent" encompass anti-hyperproliferative and antineoplastic compounds as well as other biologically therapeutic compounds.

In certain embodiments, the peptides of the invention can be covalently or non-covalently coupled to an anticancer agent, e.g., a cytotoxin or other cell proliferation inhibiting compound, in order to localize delivery of that agent to a tumor cell. For instance, the agent can be selected from the group consisting of alkylating agents, enzyme inhibitors, proliferation inhibitors, lytic agents, DNA or RNA synthesis inhibitors, membrane permeability modifiers, DNA intercalators, metabolites, dichlorethylsulfide derivatives, protein production inhibitors, toxins, viruses, ribosome inhibitors, inducers of apoptosis, and neurotoxins.

Chemotherapeutics useful as active moieties which when conjugated to peptides and of the present invention are specifically delivered to tumorigenic cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known cytotoxic agents useful in the present invention are listed, for example, in Goodman et al., The Pharmacological Basis of Therapeutics, Sixth Edition, A. G. Gilman et al, eds./Macmillan Publishing Co. New York, 1980. These include taxanes, such as paclitaxel (Taxol™) and docetaxel (Taxotere™); nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkoloids, such as vinblastine and vincristine; antibiotics, such as dactinomycin, daunorubicin, doxorubicin, bleomycin, mithramycin and mitomycin; enzymes, such as L-asparaginase; Platinum coordination complexes, such as cisplatin; substituted urea, such as hydroxyurea; methyl hydrazine derivatives, such as procarbazine; adrenocortical suppressants, such as mitotane; hormones and antagonists, such as adrencortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone). Exemplary chemotherapeutics of the invention include thapsigargin, doxorubicin, and derivatives thereof.

The thapsigargins are a group of natural products isolated from species of the umbelliferous genus *Thapsia*. The term thapsigargins has been defined by Christensen, et al., Prog. Chem. Nat. Prod., 71 (1997)130-165. These derivatives contain a means of linking the therapeutic drug to carrier moieties, including peptides and antibodies. The interactions can involve cleavage of the peptide to release the therapeutic analogs of sesquiterpene-γ-lactones. Particular therapeutic analogs of sesquiterpene-γ-lactones, such as thapsigargins, are disclosed in U.S. Pat. Nos. 6,265,540 and 6,410,514, both of which are incorporated herein in their entireties.

Thapsigargin is a sesquiterpene-γ-lactone having the structure disclosed in International Publication No. WO 98/52966. Primary amines can be placed in substituent groups pendant from either C-2 or C-8 carbon (carbons are numbered as described in International Publication No. WO 98/52966).

For example, thapsigargins with alkanoyl, alkenoyl, and arenoyl groups at carbon 8 or carbon 2, can be employed in the practice of the invention disclosed herein. Groups such as $CO—(CH=CH)_{n1}—(CH2)_{n2}—Ar—NH_2$, $CO—(CH_2)_{n2}—(CH=CH)_{n1}—Ar—NH_2$, $CO—(CH_2)_{n2}—(CH=CH)_{n1}—CO—NH—Ar—NH_2$ and $CO—(CH=CH)_{n1}—(CH_2)_{n2}—CO—NH—Ar—NH_2$ and substituted variations thereof can be used as carbon 8 substituents, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages.

In other embodiments of thapsigargin analogs, these substituent groups are represented by unsubstituted, or alkyl-, aryl-, halo-, alkoxy-, alkenyl-, amino-, or amino-substituted $CO—(CH2)n3—NH2$, where n3 is from 0 to 15, preferably 3-15, and also preferably 6-12. Particularly preferred substituent groups within this class are 6-aminohexanoyl, 7-aminoheptanoyl, 8-aminooctanoyl, 9-aminononanoyl, 10-aminodecanoyl, 11-aminoundecanoyl, and 12-aminododecanoyl. These substituents are generally synthesized from the corresponding amino acids, 6-aminohexanoic acid, and so forth. The amino acids are N-terminal protected by standard methods, for example Boc protection. Dicyclohexylcarbodiimide (DCCI)-promoted coupling of the N-terminal protected substituent to thapsigargin, followed by standard deprotection reactions produces primary amine-containing thapsigargin analogs.

The substituents can also carry primary amines in the form of an amino amide group attached to the alkanoyl-, alkenoyl-, or arenoyl substituents. For example, C-terminal protection of a first amino acid such as 6-aminohexanoic acid and the like, by standard C-terminal protection techniques such as methyl ester formation by treatment with methanol and thionyl chloride, can be followed by coupling the N-terminal of the first amino acid with an N-protected second amino acid of any type.

In a preferred embodiment, the thapsigargin analog or derivative is 8-O-(12-[L-leucinoylamino]dodecanoyl)-8-O-debutanoylthapsigargin, also referred to herein as "L12ADT".

The peptide and anticancer agent are linked directly or indirectly (by a linker) through the carboxy terminus of the peptide. The site of attachment on the anticancer agent must be such that, when coupled to the peptide, the non-specific toxicity of the drug is substantially inhibited. Thus the prodrugs should not be significantly toxic.

Drugs that interfere with intracellular protein synthesis can also be used; such drugs are known to those skilled in the art and include puromycin, cycloheximide, and ribonuclease.

Peptide and polypeptide toxins are also useful as anticancer agents, and the present invention specifically contemplates embodiments wherein the peptides of the present invention are coupled to a toxin. In certain preferred embodiments, the peptides and toxin are both polypeptides and are provided in the form of a fusion protein. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVR), gelonin (GEL), saporin (SAP), modeccin, viscumin and volkensin. In an exemplary embodiment, the protein toxin of the invention is KLAKLAKKLAKLAK (SEQ ID NO:19). In a further embodiment, the toxin is shiga toxin.

In certain embodiments, the peptides of the invention can be coupled with an agent useful in imaging tumors. Such agents include: metals, metal chelators; lanthanides; lanthanide chelators; radiometals; radiometal chelators; positron-emitting nuclei; microbubbles (for ultrasound); liposomes; molecules microencapsulated in liposomes or nanosphere; monogrystalline iron oxide ananocompounds; magnetic resonance imaging contrast agents; light absorbing, reflecting and/or scattering agents; colloidal particles; fluorophores, such as near-infrared fluorophores.

Techniques for conjugating anticancer agents and imaging agents to peptides and polypeptide are well known, see, e.g., Amon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et al., "Antibodies for Drug Delivery", in Controlled Drug Delivery (2nd Ed.), Robinson et al. (eds.), pp. 623-53 (Marcel Dekker, Inc. 1987); Thorpe, "Antibody Carriers of Cytotoxic Agents in Cancer Therapy. A Review", in Monoclonal Antibodies '84: Biological and Clinical Applications, Pinchera et al. (eds.), pp. 475-506 (1985); "Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-16 (Academic Press 1985), and Thorpe et al. (1982) "The Preparation and Cytotoxic Properties of Antibody-Toxin Conjugates", Immunol. Rev. 62:119-58.

In yet another embodiment, the peptides of the invention may be used to target microparticles, or nanoparticles, to a tumor by conjugating the peptide of the invention to the micro- or nanoparticle. The micro- or nanoparticle may comprise one or more of the anticancer or imaging agents described herein.

Pharmaceutical Compositions and Methods of Treatment

The peptides of the present invention can be used as active ingredients (together with a pharmaceutically acceptable carrier) to produce a pharmaceutical composition. The pharmaceutical composition may comprise one, or a mixture of two or more of the different peptides of the invention in an acceptable carrier.

The pharmaceutical composition can be used for the treatment of cancer. Exemplary cancers include solid tumor cancers that express PSMA, e.g., prostate cancer (hormone responsive or hormone refractory), breast, colon, lung, brain, kidney, and bladder cancer.

As used herein, the term "pharmaceutical composition" refers to the combination of an active agent (e.g., a peptide therapeutic comprising a PSMA-specific peptide) with a carrier, inert or active, making the composition especially suitable for diagnostic or therapeutic use in vitro, in vivo or ex vivo.

As used herein, the term "topically" refers to application of the compositions of the present invention to the surface of the skin and mucosal cells and tissues (e.g., alveolar, buccal, lingual, masticatory, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lautyl sulfate, isotonic and absorption delaying agents, disintrigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palnoate, pectinate, persulfate, phenylpropionate, picrate, pivalate, propionate, succinate, tartrate, thiocyanate, tosylate, undecanoate, and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The peptides, prodrugs, or pharmaceutical compositions of the present invention can be administered parenterally. Parenteral administration can include, for example, systemic administration, such as by intramuscular, intravenous, subcutaneous, or intraperitoneal injection. Compounds which resist proteolysis can be administered orally, for example, in capsules, suspensions or tablets. The compound can also be administered by inhalation or insufflations or via a nasal spray.

The peptides, prodrugs, or pharmaceutical compositions of the present invention can be administered to the individual in conjunction with an acceptable pharmaceutical carrier as part of a pharmaceutical composition for treating the diseases discussed above. Suitable pharmaceutical carriers may contain inert ingredients which do not interact with the compounds. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al, Controlled Release of Biological Active Agents, John Wiley and Sons, 1986). The formation may be also resources for administration to bone, or in the form of salve, solution, ointment, etc. for topical administration.

They may also be administered in conjunction with other modes of therapy (chemotherapy, radiotherapy) routinely used in the treatment of cancer. The peptides and prodrugs of the invention may be combined in a pharmaceutical combination formulation, or dosing regimen as combination therapy, with a second compound that has anti-hyperproliferative properties or that is useful for treating a cell proliferative disorder (e.g. cancer). The second compound of the pharmaceutical combination formulation or dosing regimen preferably has complementary activities to the compounds of the invention such that they do not adversely affect the other(s). Such molecules are suitably present in combination in amounts that are effective for the purpose intended.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities. Suitable dosages for any of the above coadministered agents are those presently used and may be lowered due to the combined action (synergy) of the newly identified agent and other chemotherapeutic agents or treatments.

The combination therapy may provide "synergy" and prove "synergistic", e.g. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, e.g. serially, whereas in combination therapy, effective dosages of two or more active ingredients are administered together.

As an example, the agent may be administered in combination with surgery to remove an abnormal proliferative cell mass. As used herein, "in combination with surgery" means that the agent may be administered prior to, during or after the surgical procedure. Surgical methods for treating epithelial tumor conditions include intra-abdominal surgeries such as right or left hemicolectomy, sigmoid, subtotal or total colectomy and gastrectomy, radical or partial mastectomy, prostatectomy and hysterectomy. In these embodiments, the agent may be administered either by continuous infusion or in a single bolus. Administration during or immediately after surgery may include a lavage, soak or perfusion of the tumor excision site with a pharmaceutical preparation of the agent in a pharmaceutically acceptable carrier. In some embodiments, the agent is administered at the time of surgery as well as following surgery in order to inhibit the formation and development of metastatic lesions. The administration of the agent may continue for several hours, several days, several weeks, or in some instances, several months following a surgical procedure to remove a tumor mass.

The subjects can also be administered the agent in combination with non-surgical anti-proliferative (e.g., anti-cancer) drug therapy. In one embodiment, the agent may be administered in combination with an anti-cancer compound such as a cytostatic compound. A cytostatic compound is a compound (e.g., a nucleic acid, a protein) that suppresses cell growth and/or proliferation. In some embodiments, the cytostatic compound is directed towards the malignant cells of a tumor. In yet other embodiments, the cytostatic compound is one that inhibits the growth and/or proliferation of vascular smooth muscle cells or fibroblasts.

Suitable anti-proliferative drugs or cytostatic compounds to be used in combination with the agents of the invention include anti-cancer drugs. Anti-cancer drugs are well known and include: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat;

Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer, Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxombicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper, Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur, Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

According to the methods of the invention, the agents of the invention may be administered prior to, concurrent with, or following the other anti-cancer compounds. The administration schedule may involve administering the different agents in an alternating fashion. In other embodiments, the agent may be delivered before and during, or during and after, or before and after treatment with other therapies. In some cases, the agent is administered more than 24 hours before the administration of the other anti-proliferative treatment. In other embodiments, more than one anti-proliferative therapy may be administered to a subject. For example, the subject may receive the agents of the invention, in combination with both surgery and at least one other anti-proliferative compound. Alternatively, the agent may be administered in combination with more than one anti-cancer drug.

A "therapeutically effective amount" is the quantity of compound which results in an improved clinical outcome as a result of the treatment compared with a typical clinical outcome in the absence of the treatment. An "improved clinical outcome" results in the individual with the disease experiencing fewer symptoms or complications of the disease, including a longer life expectancy, as a result of the treatment. With respect to cancer, an "improved clinical outcome" includes a longer life expectancy. It can also include slowing or arresting the rate of growth of a tumor, causing a shrinkage in the size of the tumor, a decreased rate of metastasis and/or improved quality of life (e.g., a decrease in physical discomfort or an increase in mobility).

The peptide and prodrugs of the invention, or compositions thereof, will generally be used in an amount effective to achieve the intended purpose. Of course, it is to be understood that the amount used will depend on the particular application.

For use to treat or prevent tumor or target cell growth or diseases related thereto, the peptides and prodrugs of the invention, or compositions thereof, are administered or applied in a therapeutically effective amount. By therapeutically effective amount is meant an amount effective to ameliorate the symptoms of, or ameliorate, treat or prevent tumor or target cell growth or diseases related thereto. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating prodrug concentration range that includes the 150 as determined in cell culture (e.g., the concentration of test compound that is lethal to 50% of a cell culture), the MIC, as determined in cell culture (e.g., the minimal inhibitory concentration for growth) or the $I_{100}$ as determined in cell culture (e.g., the concentration of peptide that is lethal to 100% of a cell culture). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

The amount of prodrug administered will, of course, be dependent on the subject being treated, on the subject's weight, the severity of the affliction, the manner of administration and the judgment of the prescribing physician.

The antitumoral therapy may be repeated intermittently. The therapy may be provided alone or in combination with other drugs, such as for example other antineoplastic entities or other pharmaceutically effective entities.

Preferably, a therapeutically effective dose of the peptides and prodrugs described herein will provide therapeutic benefit without causing substantial toxicity.

Toxicity of the peptides and prodrugs described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the prodrugs described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingi et al., 1975, In: The Pharmacological Basis of Therapeutics, Ch. 1, p. 1).

In on embodiment, the invention provides methods and compositions for treating a cell-proliferative disorder. In a preferred embodiment the cell-proliferative disorder is cancer. In one embodiment, the cancer is prostate cancer.

In another embodiment, the invention provides a method of treating cancer in a mammal having or at risk of developing cancer, comprising administering to the mammal an effective amount of a peptide or prodrug of the invention or a pharmaceutical composition comprising a peptide or prodrug of the invention.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater, more preferably, reduced by 20% or greater, more preferably, reduced by 30% or greater, more preferably, reduced by 40% or greater, even more preferably, reduced by 50% or greater, and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater, more preferably, reduced by 20% or greater, more preferably, reduced by 30% or greater, more preferably, reduced by 40% or greater, even more preferably, reduced by 50% or greater, and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater, more preferably, reduced by 20% or greater, more preferably, reduced by 30% or greater; more preferably, reduced by 40% or greater; even more preferably, reduced by 50% or greater, and most preferably, reduced by greater than 75%. Number of tumors may be measured by any reproducible means of measurement. In a preferred aspect, number of tumors may be measured by counting tumors visible to the naked eye or at a specified magnification.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater, more preferably, reduced by 20% or greater, more preferably, reduced by 30% or greater, more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving therapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population In a further aspect, treating cancer results a decrease in the mortality rate of a population of treated subjects in comparison to a population receiving therapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement In one aspect, an abnormal cellular morphology is measured by microscopy, e.g., using an inverted tissue culture microscope.

Methods of Diagnosis

The invention further provides methods of determining if a subject has cancer. In one embodiment, a peptide of the invention comprising a detectable label is administered to a subject and an image of the subject is obtained. A skilled artisan analyzes the image to determine, based on the presence, location and density of the detectable label, if a subject has cancer. Based on this diagnosis, a subject may receive a therapeutic composition of the invention alone or in combination with one or more additional anticancer therapeutics.

EXAMPLES

It should be appreciated that the invention should not be construed to be limited to the examples that are now described; rather, the invention should be construed to include any and all applications provided herein and all equivalent variations within the skill of the ordinary artisan.

Materials and Methods

Materials—M13 Phage Display System of 12 mer random library was from New England Biolabs (Beverly, Mass.). Magnetic beads with Anti-His antibody (His-MACS) were from Miltenyi Biotec (Auburn, Calif.). Drosophila Expression System (DES) was from Invitrogen (Rockville, Md.). Anti-M13-HRP Conjugate was from Amersham Pharmacia Biotech (Buckinghamshire, UK). All peptide synthesis reagents were from Anaspec (San Jose, Calif.). Unless otherwise indicated all the other reagents were from Sigma-Aldrich (St. Louis, Mo.).

Cell Lines—The LNCaP, PC-3 and DU-145 human prostate cancer cell lines (ATCC, Rockville, Md.) and CWR22R cells (Dr. John Isaacs, Johns Hopkins) were maintained by serial passage in RPMI 1640 media (Gibco, Grand Island, N.Y.) containing 10% fetal bovine serum (FBS) (Bio-Whittaker, Walkersville, Md.) in 5% CO2/95% air at 37° C.

PSMA Cloning and Expression—A PCR approach was used to amplify and attach His-6 tag (SEQ ID NO: 25) to amino terminus of extra-cellular domain of PSMA. Primers used were (forwardBglII) 5' GGAAGATCTC-ATCATCATCACCATCACCATAAATCCTC-CAATGAAGC 3' (SEQ ID NO:20) and (reverseXhoI) 5' GGCCTCGAGTCATTAGGCTACTTCACTCAAAG 3'(SEQ ID NO:21). Template amplification was performed using Pfu-polymerase (Promega, Madison) as per suggested protocol. A PCR reaction began with an initial denaturation step (94° C. for 2 mins) followed by 3 cycles of amplification (94° C. for 30 s, 40° C. for 1 min, 72° C. for 2 mins), followed by 30 cycles of amplification (94° C. for 30 s, 58° C. for 1 min, 72° C. for 2 mins), and ended with a final extension step (72° C. for 10 mins). A 2136 bp PCR fragment was purified by gel electrophoresis, digested with BglII/XhoI and cloned into pMT/BiP/V5-HisA (Invitrogen, CA) previously digested with same set of enzymes. Final construct was designated as pMT-His-PSMA.

His tagged PSMA large scale expression and purification—Schneider's S2 cells (Invitrogen) were maintained in Drosophila Expression System (DES) medium (Gibco, Rockville, Md.) supplemented with 10% FBS at 28° C. The cells were co-transfected with pMT-His-PSMA and pCoHY-GRO (19:1 ratio) selection vector using calcium phosphate-mediated transfection kit (Invitrogen). His-PSMA was purified from conditioned media by incubating with Ni-NTA resin (Qiagen, CA) in manufacturer recommended salt and imidazole concentration. PSMA was eluted using 250 mM imidazole and purity checked by SDS-PAGE Coomassie staining. Western Blot was probed with Anti-His tag [Penta-His-Horse Radish Peroxidase (HRP) Conjugate (5× His tag disclosed as SEQ ID NO: 18) from Qiagen, CA) and Anti-PSMA (Yes Biotech, Ontario, Canada] mouse monoclonal antibodies.

Phage Library Screening—Peptides from the random M13 12-mer phage library were selected using His-tagged PSMA as the target, which was then captured using magnetically labeled Anti-His Tag Antibody. To remove non-specific phage binding to Anti-His antibody and other components of the magnetic separation system, the library was depleted 2 times with the His-MACS system. First Round of Screening: The final eluate from negative screening was incubated with 0.8 μgs of PSMA for 30 mins at room temperature. 50 uls of His-MACS were added and allowed to bind for 30 mins at room temperature. The incubation mixture was loaded onto a MACS column and washed twice with 1 ml of PBS/0.1% Tween 20 (PBST). Beads containing PSMA bound to phage were collected and amplified using PhD Kit protocol (NEB, Auburn, Mass.). Second Round Screening: Negative screening was repeated as above except with more BSA (0.5%) and longer incubation (1 hr at 4° C.). $10^{10}$ pfu from the first round of screen were then incubated with PSMA in 1% BSA for 6 hrs at 4° C. His-MACS in 3% BSA were incubated for 30 mins and bound phages were collected and amplified as in round one. For third round screening the same method was used except Mouse IgG solution (100 μgs/ml) was added to the blocking solution. Individual phage were selected and sequenced after third round of screening.

Peptide Synthesis—Peptides were synthesized using standard solid phase Fmoc chemistry on Wang resin as previously described (20). Dimeric peptide was synthesized by coupling Fmoc-Lys-(Fmoc) to Lys-(ε-Biotin or FITC)-Wang resin. Peptides were purified using reverse phase-high pressure liquid chromatography and sequences confirmed by MALDI-TOF mass spectroscopy.

PSMA Enzymatic Assay The enzymatic activity assay for PSMA was adapted as previously described by Tiffany et al. (21). PSMA (5 nM) incubated with or without peptides was added to PSMA assay buffer (10 mM $CoCl_2$, 50 mM Tris, pH 7.4). Following a 30 mins incubation at 37° C., N-acetyl-aspartyl-3H glutamate (3H-NAAG) (NEN, Boston, Mass.) was added to final concentration of 25 nM and reactions incubated for 15 mins at 37° C. Data were collected during linear phase of hydrolysis (i.e. less than 20% cleavage of total substrate).

Phage ELISA—The phage displaying a specific peptide was amplified and purified and peptide display confirmed by DNA sequencing. The titer value of the specific purified phage was determined and three different dilutions were prepared in 1% BSA in PBST. PSMA (0.625 μgs) was coated on 96 well polystyrene ELISA plates blocked with 3% BSA in PBST at 37° C. for 2 hrs. Phage dilutions were incubated for 1 hr at room temperature. For competitive assay, PSMA phages at $10^{10}$ pfu/ml were first incubated at room temperature for 1 hr with 500 nM PSMA. Blocking solution was then removed from wells and phage dilution were incubated for 1 hr at room temperature. After 7× washing, anti-M13-HRP conjugate (1:500) in 3% BSA in PBST was incubated for 30 mins. After a second wash (7×PBST) the HRP substrate O-Phenylenediamine Dihydrochlroride (OPD) was added and absorbance measured at 450 nm.

Reverse ELISA—Streptavidin coated 96 well plates were blocked with 2% BSA in PBST for 1 hr. After washing, biotinylated peptide monomer and the dimeric peptide were incubated at a final concentration of 25 μM for 2 hrs. After washing, PSMA 100 nM in 3% BSA was incubated for 2 hrs at RT. Wells were washed 6× with PBST and Anti-PentaHis-HRP conjugate (5×His tag disclosed as SEQ ID NO: 18) (1:1000) in 3% BSA was incubated for 1 hr. Substrate 2,2'-Azino-bis(3-Ethylbenzthiazoline-6-Sulfonic Acid) (ABTS) was added and bsorbance was measured at 405 nm after 30 mins.

Structural Modeling: The MOE program (CCG, Montreal) was used to build monomeric as well as dimeric peptide. The minimization of the dimer was performed in the presence of Cobalt cation using OPLS-AA force field. The continuum solvent model was used to mimic the solvent effects. GOLD v3.0 program (CCDC, UK) was used to dock the peptide moiety in the binding site of PSMA. The crystal structure of PSMA dimer [PDB Code: 1Z8L] was used to extract the coordinates for the protein monomer for subsequent docking. GOLD program uses a genetic docking program for flexible docking of ligands into protein binding sites. This program has been shown to produce accurate results for many protein-ligand systems including metalloproteases. The default parameters in the GOLD program were used to perform all docking runs. The binding site was defined by a radius of 25 A from the catalytic site which is large enough for the peptide to sample all the binding sites in the vicinity of catalytic site.

Results

Identification of PSMA Binding Peptides

To screen for peptides that bind only to the extracellular domain of PSMA recombinant PSMA lacking the transmembrane and intracellular domain was generated. Purified His-PSMA ran as single band on a Coomassie stained gels and was visualized by western blotting using anti-PSMA mouse monoclonal antibody (data not shown). His-PSMA released $^3$H Glu from the $^3$H NAAG substrate at a rate of 61±8 nmoles $^3$H Glu/min/mg protein. This purified, enzymatically active His-PSMA was used for all subsequent binding experiments.

To decrease the selection of non-specific low affinity binders, phage screening was performed in solution and incorporated negative screening steps using other selection components (i.e. antibodies, magnetic beads, etc.) to remove many background binders (22). Thus, for this study the phage library was incubated with magnetically labeled Anti-His$_6$ (SEQ ID NO: 25) antibody after every round of selection. After negative selection steps, His-PSMA was incubated with the phage library and phages bound to His-PSMA were captured using magnetically labeled Anti-His$_6$ (SEQ ID NO: 25) antibody, FIG. 1.

The number of bound phages increased with each round of selection. After the second round of screening, the number of bound phage increased by over three orders of magnitude but increased by less than an order of magnitude after the third round, FIG. 1. Therefore, after this third round, 40 individual phages were sequenced, FIG. 1. More than 30% of the sequenced phages were represented by the peptide sequence WQPDTAHHWATL (SEQ ID NO:1). A second sequence, HNAYWHWPPSMT (SEQ ID NO:2), was found in more than 15% of the sequenced peptides. Ten of sixteen sequences contained the motif HHX while one third (6/18) of the peptides contained a three amino acid sequence HHW, WHW, HWH, or HWW. 16 of 18 sequences had at least one proline residue, whereas 11/18 had two or more proline residues (range 2-5). None of the phage had similarity to sequences known to bind to magnetic particles (22). None of the sequences contained multiple acidic amino acids and therefore were unlikely to be PSMA substrates.

Selectivity of binding of WQPDTAHHWATL (SEQ ID NO:1) phage—Two different types of ELISA experiments were performed to investigate the selectivity of WQPDTAHHWATL (SEQ ID NO:1) phage binding to PSMA. First, phage binding to immobilized His-PSMA was compared to binding to immobilized BSA, FIG. 2A. In this Phage ELISA, increasing amounts of WQPDTAHHWATL (SEQ ID NO:1) phage showed higher binding to immobilized PSMA compared to BSA. The optimal binding differential occurred at a dilution of $10^{10}$ pfu/ml with almost 10-fold higher binding to PSMA compared to BSA, FIG. 2A.

In a second assay, soluble PSMA was used to compete with phage ($10^{10}$ pfu/ml) binding to immobilized proteins, FIG. 2B. In this assay, 500 nM of soluble His-PSMA inhibited binding of WQPDTAHHWATL (SEQ ID NO:1) phage to immobilized PSMA by greater than 60%. In contrast, soluble BSA had no effect on binding to immobilized PSMA. Additionally, soluble PSMA did not appreciable alter non-specific binding of phage to immobilized BSA. These results support the conclusion that phage displaying the WQPDTAHHWATL (SEQ ID NO:1) peptide bind selectively to PSMA.

Soluble Synthetic WQPDTAHHWATL (SEQ ID NO:1) peptide binds selectively to PSMA—On the basis of the phage binding results, the WQPDTAHHWATL (SEQ ID NO:1) peptide was synthesized with biotin coupled to the C-terminus. The C-terminus was chosen for tagging because the peptide sequences were originally displayed on phage coat surface as N-terminus fusions, suggesting that the N-terminus is involved in binding to PSMA. Incubation of the biotinylated WQPDTAHHWATL (SEQ ID NO:1) peptide with immobilized PSMA or BSA demonstrated significantly higher binding to PSMA at peptide concentrations of 50 μM and 500 μM, FIG. 3A. In contrast, a control consisting of a positively charged 12 amino acid peptide showed higher overall binding to both proteins but no specific binding to immobilized PSMA compared to BSA, (inset FIG. 3A) demonstrating that binding observed with the WQPDTAHHWATL (SEQ ID NO:1) peptide is not based merely on presence of positively charged residues in the peptide sequence. These results, therefore, suggest that the WQPDTAHHWATL (SEQ ID NO:1) peptide is a low affinity binding peptide that is relatively selective for PSMA.

Dimerization of WQPDTAHHWATL (SEQ ID NO:1) peptide markedly enhances binding to PSMA and inhibition of enzymatic activity—Screening phage-based peptide libraries to identify sequences that bind to non-peptide binding proteins (non-receptors) often yields low affinity binding ligands (22). Previous studies have demonstrated that dimerization of peptides through the use of a lysine residue at the C-terminus can markedly increase binding affinity due to an avidity effect (20,23,24). Therefore, a dimeric form of the WQPDTAHHWATL (SEQ ID NO:1) peptide was synthesized containing biotin at the C-terminus. The biotinylated monomeric and dimeric peptides were immobilized on streptavidin coated wells and a reverse ELISA was performed by incubation with purified soluble His-PSMA (100 nM). In this assay His-PSMA bound significantly better to the dimeric peptide compared to the monomeric FIG. 3B.

WQPDTAHHWATL (SEQ ID NO:1) peptide inhibits PSMA's enzyme activity—Functionally, PSMA has been classified as a glutamate carboxypeptidase II (25) with activity as both an N-acetylated α-linked acidic dipeptidase (NAALADase) (26) and as a pteroyl poly-γ-glutamyl carboxypeptidase (i.e. folate hydrolase) (27). PSMA's NAALADase activity can be easily measured by monitoring hydrolysis of the substrate $^3$H NAAG, which is known to be have very high affinity and specificity for PSMA ($K_m$=430 nM and a $k_{cat}$=0.6 s$^{-1}$ of protein/min) (21). Therefore, the monomeric and dimeric WQPDTAHHWATL (SEQ ID NO:1) peptides were incubated initially with PSMA for 30 mins and then $^3$H NAAG substrate was added to prevent any NAAG hydrolysis before the peptide is able to bind to PSMA. Control peptides included the QMARIPKRLARH (SEQ ID NO: 22) peptide and a short peptide HHWA (SEQ ID NO: 26) containing the apparent consensus motif from the phage display. In this study, the monomeric WQPDTAHHWATL (SEQ ID NO:1) peptide was able to inhibit NAAG hydrolysis with an IC$_{50}$ of 23 μM, (FIG. 4). In comparison, the dimeric WQPDTAHHWATL (SEQ ID NO:1) peptide inhibited NAAG hydrolysis with an IC$_{50}$ of 2.2 μM, (FIG. 4). In contrast, excess control peptides QMARIPKRLARH (SEQ ID NO:22) and HHWA (SEQ ID NO: 26) had no effect on NAAG hydrolysis at 100 μM concentration (i.e. <5% inhibition of activity after 30 min incubation). In a second experiment, cell lysates from PSMA-producing LNCaP were used instead of purified recombinant His-PSMA. PSMA also was inhibited by the monomeric WQPDTAHHWATL (SEQ ID NO:1) peptide at 60 μM in this assay, confirming that the WQPDTAHHWATL (SEQ ID NO:1) peptide could also inhibit the full length membrane bound form of PSMA.

Binding of WQPDTAHHWATL (SEQ ID NO:1) peptides to PSMA-expressing cell lines—To analyze peptide binding to membrane bound PSMA, fluorescently labeled peptides were synthesized by coupling FITC to the C-terminus of either the monomeric or dimeric peptide. Previously we had characterized PSMA expression and enzymatic activity of human prostate cancer cell lines and, based on this analysis, selected two lines, LNCaP and CWR22R that produced measurable levels of enzymatically active PSMA and two lines, PC-3 and DU145 that did not. WQPDTAHHWATL (SEQ ID NO:1) monomeric and dimeric peptides were incubated with these prostate cancer cell lines at varying concentrations (i.e. 1, 5, 10, 50 μM) in tissue culture media containing 1% fetal bovine serum as a blocking agent In this assay, binding of the monomeric WQPDTAHHWATL (SEQ ID NO: 1) peptide above background autofluorescence could not be observed at any of the tested concentrations, FIG. 5. In contrast, cell binding of the dimeric WQPDTAHHWATL (SEQ ID NO:1) peptide could be easily visualized at concentrations as low as 5 μM, FIG. 5. Labeled, dimeric peptide bound to a similar degree to both CWR22R and LNCAP. In contrast, no significant binding of fluorescent labeled WQPDTAHHWATL (SEQ ID NO:1) dimeric peptide above background to non-PSMA expressing prostate cancer cells was observed, FIG. 5.

Modeling the structure of the dimeric peptide—Previously it has been proposed that PSMA is active only in its dimeric form (7) which possesses two catalytic sites which could potentially be targeted better by a dimeric peptide that bridged the two binding sites. Experimentally, we demonstrated that the dimeric version of the peptide is a ~10-fold better inhibitor of PSMA than the monomer. Therefore, we performed a careful analysis of the crystal structure of the PSMA dimer [PDB Code: 1Z8L] to evaluate whether each arm of the dimeric peptide could bind separately to each protein monomer in the crystal structure. This type of binding of a dimeric peptide to a protein dimer has been observed before in the case of an erythropoietin mimetic peptide binding to the dimer interface of the erythropoietin receptor (22). The crystal structure analysis of PSMA, however, revealed that the catalytic binding sites of each protein monomer face opposite to each other with the distance between two similar $Zn^{2+}$ atoms in the catalytic site of each monomer being 56. Thus, the orientation of the catalytic sites and the large distance between them rule out the possibility of this 12 amino acid dimeric peptide binding the catalytic site of both protein monomers simultaneously.

In order to understand the role of peptide secondary structure on the PSMA inhibition, we have modeled the solution structure of dimeric peptide, FIG. 6A. In this model, two arms of peptide are brought close to each other via coordination of a divalent cobalt cation by two histidines located on each arm. Due to steric considerations, the other two histidine residues can not participate in the metal coordination at the same time and remain solvent exposed whereby they are free to coordinate with other metal ions. This possibly explains why the higher concentration of cobalt results in the aggregation and precipitation of the peptide substrates. The energy minimized structure adopts a beta-turn like loop on the N-terminal side of each arm which brings the tryptophan and asparatic sidechains on the same side. The beta-turn like structure at the N-terminal of peptide agrees with observation that the N-terminal sequence QPD is similar to non-native beta-turn sequence (NPDG) which has been implicated in nucleating the formation of a beta-hairpin in peptides derived from N-terminal of ubiquitin (28).

The beta-turn like structure of the peptide at the N-terminus is consistent with the shape of the catalytic binding cavity which is narrow and covers much less surface area than the entire PSMA dimer surface, FIG. 6B. To discover the binding mode of N-terminal residues in the dimeric peptide, we docked the WQPDTA (SEQ ID NO: 23) motif in the catalytic site of PSMA using the program GOLD v3.0. To preclude any personal bias, the binding mode with the highest GOLD-score (47.8) was chosen to be the best representative of the true binding mode.

The catalytic site of PSMA is polar mostly due to an arginine patch where a series of arginine residues are clustered within 4.5 Å of each other and 6-12 Å away from the nearest Zinc atom. FIG. 6C presents the binding mode of the WQPDTA (SEQ ID NO: 23) motif in the catalytic site. W1 of the peptide is docked opposite to the arginine patch in a shallow hydrophobic pocket located at the interface of apical and helical domain formed mainly by Phe-209, Tyr-700 and the aliphatic side-chain of Lys-207. This explains why a hydrophobic residue such as W1 can be accommodated in a mostly polar binding site. The free amine at the N-terminal is in a position to make a hydrogen bond with Tyr-234 and Gln-254. The carboxy side-chain of D4 is oriented towards the catalytic water and is the closest to the Zinc atoms. The side-chain of D4 is docked in the arginine patch making a hydrogen bond with Arg-463 which might be critical for the overall binding of the peptide. The C-terminal part of the WQPDTA (SEQ ID NO: 23) motif including T5 and A6 docks in a groove formed at the interface of Helical and protease domain. The side-chain hydroxyl of T5 residue is in perfect position to make a hydrogen bond with Asp-465.

The C-terminal of the WQPDTA (SEQ ID NO: 23) motif lies above Arg-511 and is oriented towards groove located between helical and protease domain. This suggests that the HHWATL (SEQ ID NO: 27) motif at the C-terminal of docked motif will be positioned outside the catalytic site towards this groove. The positioning of the C-terminus of the docked motif validates the authenticity of the unbiased binding mode as, even though the docking calculations were blind to the presence of HHWATL (SEQ ID NO: 27) motif at the C-terminal, the binding mode still allowed for the presence for extra residues at the C-terminal.

Phage display of random peptide libraries has been used successfully in a number of applications that include identification of protein binding ligands, optimization of antibody binding and identification of substrates for proteases (29-32). The goal of this study was to use a phage library containing a random linear peptide displayed at the amino terminus of the coat protein III to identify peptides which bind specifically to the prostate tissue differentiation protein and cancer marker PSMA.

Since the intended target for this targeting strategy is the extracellular portion of the PSMA protein, in this study we generated a soluble, His-tagged PSMA protein that lacked the transmembrane and intracellular domains of PSMA. We employed a solution phase screening of phage display library of 12 amino acid long peptides to select for peptides binding to recombinant His tagged PSMA. Such solution screening promotes affinity discrimination and yields peptides with higher binding affinities compared to solid-phase panning methodologies (22).

The peptide sequences obtained from this screening were compared to the known target-unrelated peptides frequently recovered in the screening of phage-displayed random peptide libraries with antibodies (34). Also there was no sequence similarity to known peptides that bind to magnetic particles (22). Forty selected phages were sequenced and one sequence, WQPDTAHHWATL (SEQ ID NO: 1), was identified which contributed to more than 30% of the sequenced phages. In addition, 23/40 of the peptide sequences contained on of three tripeptide motifs HHW, WHW, HWH. The peptide motif HHX was observed in ~60% of the unique sequences or 25/40 total sequences. This dihistidine peptide motif had also emerged as part of a consensus PSMA binding sequence identified previously in a phage display-based screening of a cyclic 6 amino acid peptide library (35).

In this study the WQPDTAHHWATL (SEQ ID NO:1) peptide demonstrated selectivity of binding to PSMA based on ELISA based plate assays and the binding of this peptide to surface bound PSMA could be competed off by soluble PSMA. The $IC_{50}$ for inhibition of PSMA's NAALADASE activity was 23 µM. This type of low affinity non-optimized binding is of the same order of magnitude observed in other studies using phage display to select peptide binding to non-receptor proteins. Previously, it had been demonstrated by many groups, including our own, that the peptide binding affinity can be improved by increasing the binding avidity through use of multivalent binding strategies such as dimeric or tetrameric peptides or streptavidin-biotinylated peptide tetramers (20,23,24). Dimerization of the WQPDTAHHWATL (SEQ ID NO:1) peptide resulted in significant enhancement of PSMA binding compared to the monomeric form.

The dimeric peptide also demonstrated inhibition of PSMA enzymatic activity at 10-fold lower concentrations. In addition, binding of a fluorescently labeled dimeric peptide selectively to PSMA-producing prostate cancer cells compared to non-PSMA producing cells could be easily visualized at a peptide concentration of 5 µM, whereas no binding of the fluorescently tagged monomeric peptide was observed at concentrations up to 50 µM. These results support prior observations that binding characteristics of peptides identified by phage display techniques can be greatly enhanced through generation of dimeric or multivalent peptides.

The sequence analysis of all the peptides selected by the phage display reveals that there is an over abundance of histidines and prolines. The presence of histidines in most of the peptides is intriguing as histidines residues are known to chelate divalent metal ions including zinc. The PSMA catalytic binding site contains two zinc ions which can be chelated by these histidines leading to inactivation of the enzyme. However, the experimental data appears to exclude this mechanism for binding as the short peptide HHWA (SEQ ID NO: 26) did not possess any inhibitory potency towards PSMA.

Histidines have also been found abundant in earlier phage display binding studies directed towards other non-metalloprotease systems (36-38). These observations led us to hypothesize that the histidines in the WQPDTAHHWATL (SEQ ID NO:1) peptide are not directly involved in PSMA binding. Rather, they help the dimeric peptide chains adopt a particular configuration that is favorable for PSMA binding. This can be achieved via histidines interacting with the divalent cations abundant in the assay buffers such as cobalt and modulating the structure of the peptide especially when in the dimeric form. This hypothesis is strongly favored by an earlier NMR study on the PSMA substrate and neurodipeptide NAAG that concluded that metal binding has important consequences for the solution structure of these dipeptides and their ability to act as PSMA substrates (39). For the WQPDTAHHWATL (SEQ ID NO:1) peptide, the dimeric form brings four histidines into close vicinity. This can lead to efficient coordination of a divalent cation such as cobalt by the dimer and result in the adoption of a favorable configuration for binding and subsequent inhibition of PSMA.

Modeling of WQPDTAHHWATL (SEQ ID NO: 1) sequence demonstrated that the proline in the peptide produces a beta-turn like structure at the N-terminus that is consistent with the shape of the narrow catalytic binding cavity of PSMA. The binding of peptides to such a cavity will result in severe torsion in the peptide chain and loss of conformational flexibility resulting in a high entropic penalty for flexible peptides. Therefore, the dimeric peptide with the combination of divalent cation complex formation with dihistidines and the proline-induced beta turns results in stabilization of the peptide into a less flexible, more entropically favorable conformation that enhances binding characteristics compared to the monomeric peptide.

The results of these experiments demonstrate that the dimerization of the PSMA-binding peptide enhances PSMA inhibition ~10-fold compared to the monomeric peptide. Modeling studies suggest that this enhanced binding is due to stabilization of the peptide into a less flexible conformation. This stabilization is similar to what occurs with cyclization of peptides using flanking cysteine residues.

REFERENCES

1. Fair W R, Israeli R S, Heston W D. Prostate-specific membrane antigen. Prostate. 1997; 32:140-8.
2. Kawakami M, Nakayama J. Enhanced expression of prostate-specific membrane antigen gene in prostate cancer as revealed by in situ hybridization. Cancer Res 1997; 57:2321-4.
3. Silver D A, Pellicer I, Fair W R, et al. Prostate-specific membrane antigen expression in normal and malignant human tissues. Clin Cancer Res 1997; 3:81-5.
4. Bander N H, Milowsky M I, Nanus D M, et al. Phase I trial of 177lutetium-labeled J591, a monoclonal antibody to prostate-specific membrane antigen, in patients with androgen-independent prostate cancer. J Clin Oncol 2005; 23:4591-601.
5. Mhaka A, Gady A M, Rosen D M, et al. Use of methotrexate-based peptide substrates to characterize the substrate specificity of prostate-specific membrane antigen (PSMA). Cancer Biol Ther 2004; 3:551-8.
6. Davis M I, Bennett M J, Thomas L M, et al. Crystal structure of prostate-specific membrane antigen, a tumor marker and peptidase. Proc Natl Acad Sci U S A 2005; 102:5981-6.
7. Schulke N, Varlamova O A, Donovan G P, et al. The homodimer of prostate-specific membrane antigen is a functional target for cancer therapy. Proc Natl Acad Sci U S A. 2003; 100:12590-5.
8. O'Keefe D S, Bacich D J, Heston W D. Comparative analysis of prostate-specific membrane antigen (PSMA) versus a prostate-specific membrane antigen-like gene. Prostate. 2004 Feb. 1; 58(2):200-10.
9. Cunha A C, Weigle B, Kiessling A, et al. Tissue-specificity of prostate specific antigens: Comparative analysis of transcript levels in prostate and non-prostatic tissues. Cancer Lett. 2006 18; 236:229-38.
10. Dumas F, Gala J L, Berteau P, et al. Molecular expression of PSMA mRNA and protein in primary renal tumors. Int J Cancer 1999; 80:799-803.
11. Gala J L, Loric S, Guiot Y, et al. Expression of prostate-specific membrane antigen in transitional cell carcinoma of the bladder: prognostic value? Clin Cancer Res 2000; 6:4049-54.
12. Liu H, Moy P, Kim S, et al. Monoclonal antibodies to the extracellular domain of prostate-specific membrane antigen also react with tumor vascular endothelium. Cancer Res 1997; 57:3629-34.
13. Chang S S, Reuter V E, Heston W D, et al. Five different anti-prostate-specific membrane antigen (PSMA) antibodies confirm PSMA expression in tumor-associated neovasculature. Cancer Res 1999; 59:3192-8.
14. Huang X, Bennett M, Thorpe P E. Anti-tumor effects and lack of side effects in mice of an immunotoxin directed against human and mouse prostate-specific membrane antigen. Prostate 2004; 61:1-11
15. Nanus D M, Milowsky M I, Kostakoglu L, et al. Clinical use of monoclonal antibody HuJ591 therapy: targeting prostate specific membrane antigen. J Urol 2003; 170:S84-8; discussion S88-9.
16. Leuschner C, Enright F M, Gawronska-Kozak B, et al. Human prostate cancer cells and xenografts are targeted and destroyed through luteinizing hormone releasing hormone receptors. Prostate 2003; 56:239-49.
17. Schally A V, Nagy A. New approaches to treatment of various cancers based on cytotoxic analogs of LHRH, somatostatin and bombesin. Life Sci 2003; 72:2305-20.
18. Grifinan M, Trepel M, Speece P, et al. Incorporation of tumor-targeting peptides into recombinant adeno-associated virus capsids. Mol Ther 2001; 3:964-75.
19. Barbas C. F., Burton D. R., Scott J. K. and Silverman G. J. (2000) Phage Display: A Laboratory Manual. Cold Spring Harbor Laboratory Press, Cold Spring Harbor, N.Y.
20. Aggarwal S, Janssen S, Wadkins R M, et al. A combinatorial approach to the selective capture of circulating malignant epithelial cells by peptide ligands. Biomaterials 2005; 26:6077-86.
21. Tiffany C W, Lapidus R G, Merion A, et al. Characterization of the enzymatic activity of PSM: comparison with brain NAALADase. Prostate 1999; 39:28-35.

22. Gebhardt K, Lauvrak V, Babaie E, et al. Adhesive peptides selected by phage display: characterization, applications and similarities with fibrinogen. Pept Res 1996; 9:269-78.
23. Cwirla S E, Balasubramanian P, Duffin D J, et al. Peptide agonist of the thrombopoietin receptor as potent as the natural cytokine. Science 1997; 276:1696-9.
24. Wrighton N C, Balasubramanian P, Barbone F P, et al. Increased potency of an erythropoietin peptide mimetic through covalent dimerization. Nat Biotechnol 1997; 15:1261-5.
25. Luthi-Carter R, Barczak A K, Speno H, et al. Molecular characterization of human brain N-acetylated alpha-linked acidic dipeptidase (NAALADase). J Pharmacol Exp Ther. 1998; 286:1020-5.
26. Carter R E, Feldman A R, Coyle J T. Prostate-specific membrane antigen is a hydrolase with substrate and pharmacologic characteristics of a neuropeptidase. Proc Natl Acad Sci U S A 1996; 93:749-53.
27. Pinto J T, Suffoletto B P, Berzin T M, et al. Prostate-specific membrane antigen: a novel folate hydrolase in human prostatic carcinoma cells. Clin Cancer Res 1996; 2:1445-51.
28. Jourdan M, Griffiths-Jones S R, Searle M S. Folding of a beta-hairpin peptide derived from the N-terminus of ubiquitin. Conformational preferences of beta-turn residues dictate non-native beta-strand interactions. Eur J Biochem 2000; 267:3539-48.
29. Arap W, Kolonin M G, Trepel M, et al. Steps toward mapping the human vasculature by phage display. Nat Med 2002; 8:121-7.
30. El-Mousawi M, Tchistiakova L, Yurchenko L, et al. A vascular endothelial growth factor high affinity receptor I-specific peptide with antiangiogenic activity identified using a phage display peptide library. J Biol Chem 2063; 278:46681-91.
31. Pan W, Amone M, Kendall M, et al. Identification of peptide substrates for human MMP-11 (stromelysin-3) using phage display. J Biol Chem 2003; 278:27820-7.
32. Smith G P, Petrenko V A. Phage Display. Chem Rev 1997; 97:391-410.
33. Aina O H, Sroka T C, Chen M L, et al. Therapeutic cancer targeting peptides. Biopolymers 2002; 66:184-99.
34. Menendez A, Scott J K. The nature of target-unrelated peptides recovered in the screening of phage-displayed random peptide libraries with antibodies. Anal Biochem 2005; 336: 145-57.
35. Lupold S E, Rodriguez R. Disulfide-constrained peptides that bind to the extracellular portion of the prostate-specific membrane antigen. Mol Cancer Ther 2004; 3:597-603.
36. Dreier B, Segal D J, Barbas C F 3rd. Insights into the molecular recognition of the 5'-GNN-3' family of DNA sequences by zinc finger domains. J Mol Biol 2000; 303: 489-502.
37. Eteshola E, Brillson L J, Lee S C. Selection and characteristics of peptides that bind thermally grown silicon dioxide films. Biomol Eng 2005; 22:201-4.
38. Rodi D J, Soares A S, Makowski L. Quantitative assessment of peptide sequence diversity in M13 combinatorial peptide phage display libraries. J Mol Biol 2002; 322: 1039-52.
39. Lannom H K, Dill K, Denarie M, et al. 13C n.m.r. study of the structure and the metal ion binding sites of neuropeptides composed of L-Asp and L-Glu. Int J Pept Protein Res 1986; 28:67-78.
40. Oliver A J, Wiest O, Helquist P, et al. Conformational and SAR analysis of NAALADase and PSMA inhibitors. Bioorg Med Chem 2003; 11:4455-61.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated peptide comprising WQPDTAHHWATL (SEQ ID NO:1), wherein the peptide is capable of binding to PSMA.

2. The isolated peptide of claim 1, wherein the peptide consists of the amino acid set forth as SEQ ID NO:1.

3. The isolated peptide of claim 1, wherein the peptide further comprises the second amino acid sequence set forth as SEQ ID NO:1.

4. The isolated peptide of claim 1, further comprising one or more additional amino acid sequences set forth as SEQ ID NOs: 2-17.

5. The isolated peptide of claim 1, wherein the peptide is linked to an imaging agent.

6. The isolated peptide of claim 5, wherein the imaging agent is a radiolabel.

7. An isolated peptide comprising a first amino acid sequence as set forth in SEQ ID NO:1 and a second amino acid sequence as set forth in SEQ ID NO:1, wherein the first and second amino acid sequences are connected by a linker, and wherein the peptide is capable of binding to PSMA.

8. An isolated peptide comprising SEQ ID NO: 1 and a second amino acid sequence selected from the group consisting of SEQ ID NO: 2-17, wherein the first and second amino acid sequences are connected by a linker, wherein the peptide is capable of binding to PSMA.

9. The isolated peptide of claim 8, wherein the linker is an amino acid, peptide, chemical moiety, diamine, or polyglycol.

10. A composition comprising the isolated peptide of claim 1 and a carrier.

11. A kit comprising the isolated peptide of claim 1 and instructions for use.

12. A kit for determining if a subject has a prostate cancer comprising the isolated peptide of claim 5, and instructions for use.

* * * * *